United States Patent [19]

Luce et al.

[11] Patent Number: 4,519,710

[45] Date of Patent: May 28, 1985

[54] COLORIMETER

[75] Inventors: Robert S. Luce, Los Altos; Ross A. Quinn, Los Altos Hills; Leroy S. Rowley, San Jose, all of Calif.

[73] Assignee: Lockheed Missiles & Space Company, Inc., Sunnyvale, Calif.

[21] Appl. No.: 477,226

[22] Filed: Mar. 21, 1983

[51] Int. Cl.³ .............................................. G01J 3/50
[52] U.S. Cl. .................................. 356/411; 356/412; 356/413; 356/414
[58] Field of Search ............... 356/402, 407, 409, 410, 356/411, 412, 413, 414, 416, 418, 432, 436, 437, 440, 246

[56] References Cited

U.S. PATENT DOCUMENTS

| | | | |
|---|---|---|---|
| 3,740,155 | 6/1973 | Keller et al. | 356/409 |
| 3,743,426 | 7/1973 | Steinberg | 356/418 |
| 4,066,362 | 1/1978 | Carter | 356/409 |
| 4,099,882 | 7/1978 | Andren et al. | 356/414 |

Primary Examiner—F. L. Evans
Attorney, Agent, or Firm—John J. Morrissey

[57] ABSTRACT

A colorimeter for continuously monitoring the concentration of an ionic species in an aqueous solution comprises a source 30 of optical radiation, a flow cell 10 including three flow chambers 11, 12 and 13 interconnected so that a sample of the solution can pass through each flow chamber in succession, and photodetector devices 41, 42 and 43 positioned to respond to radiation transmitted through the solution in the flow chambers 11, 12 and 13, respectively. The lengths of the three flow cells are different from each other to provide a continuous real-time calibration check based upon photodetector responses to radiation transmitted through different quantities of the solution. Electronic circuitry interconnecting the radiation source 30 and the photodetector devices 41, 42 and 43 maintains the intensity of the radiation emitted by the source 30 at a substantially constant value.

13 Claims, 8 Drawing Figures

U.S. Patent   May 28, 1985   Sheet 1 of 6   4,519,710
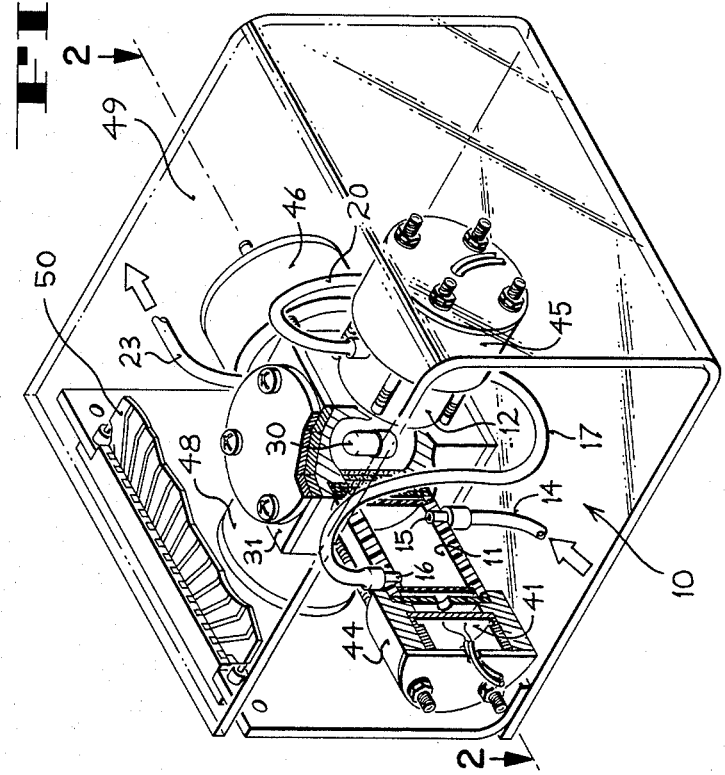
FIG_1
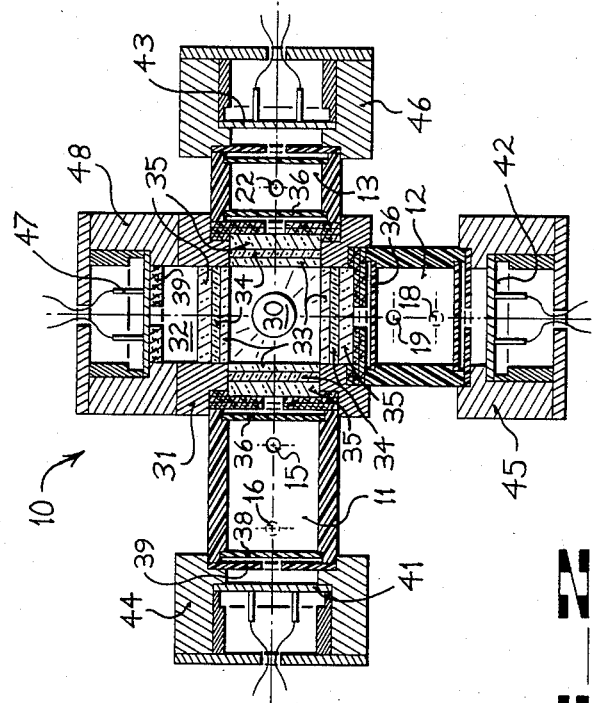
FIG_2

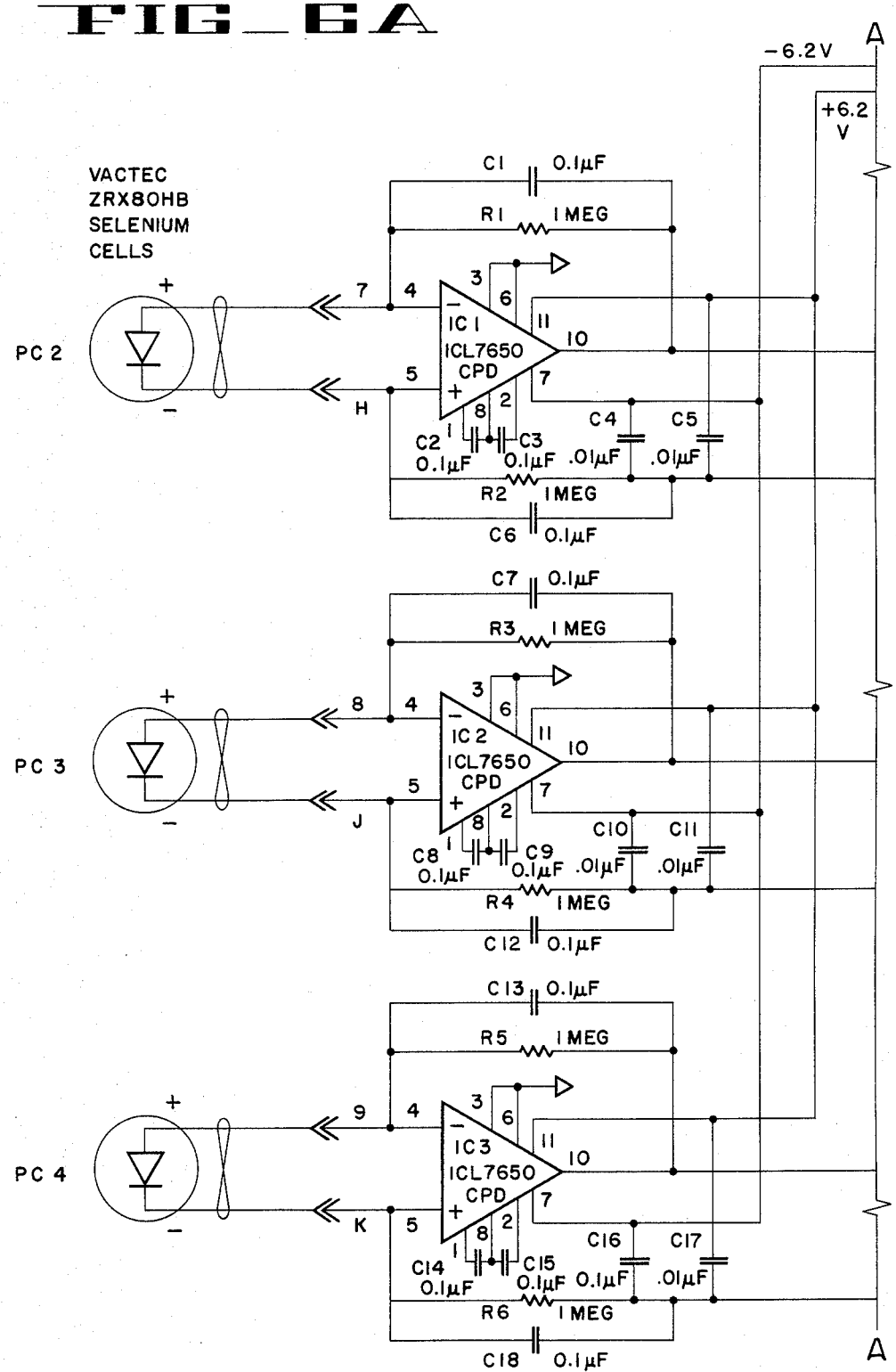
FIG_6A

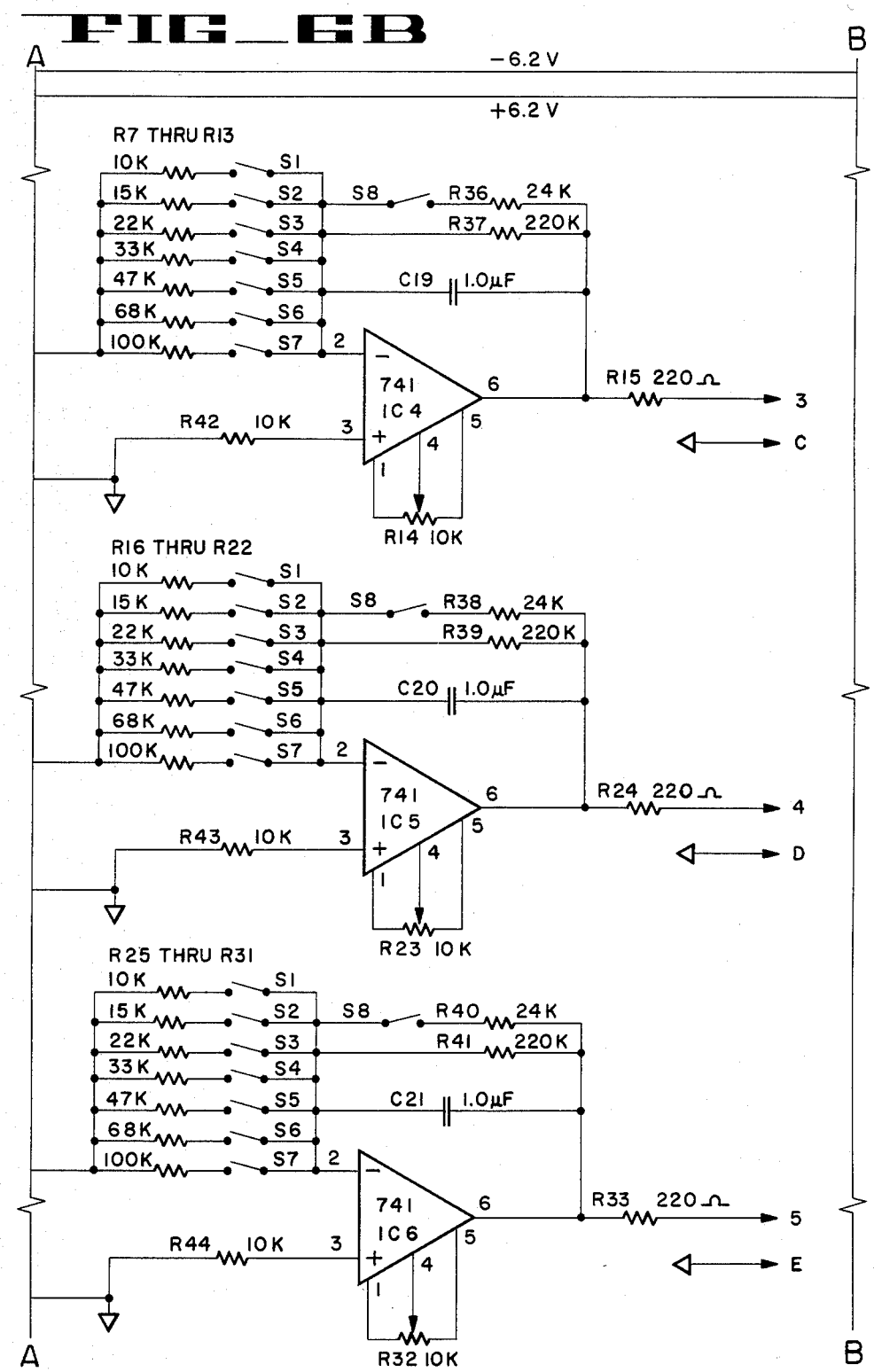

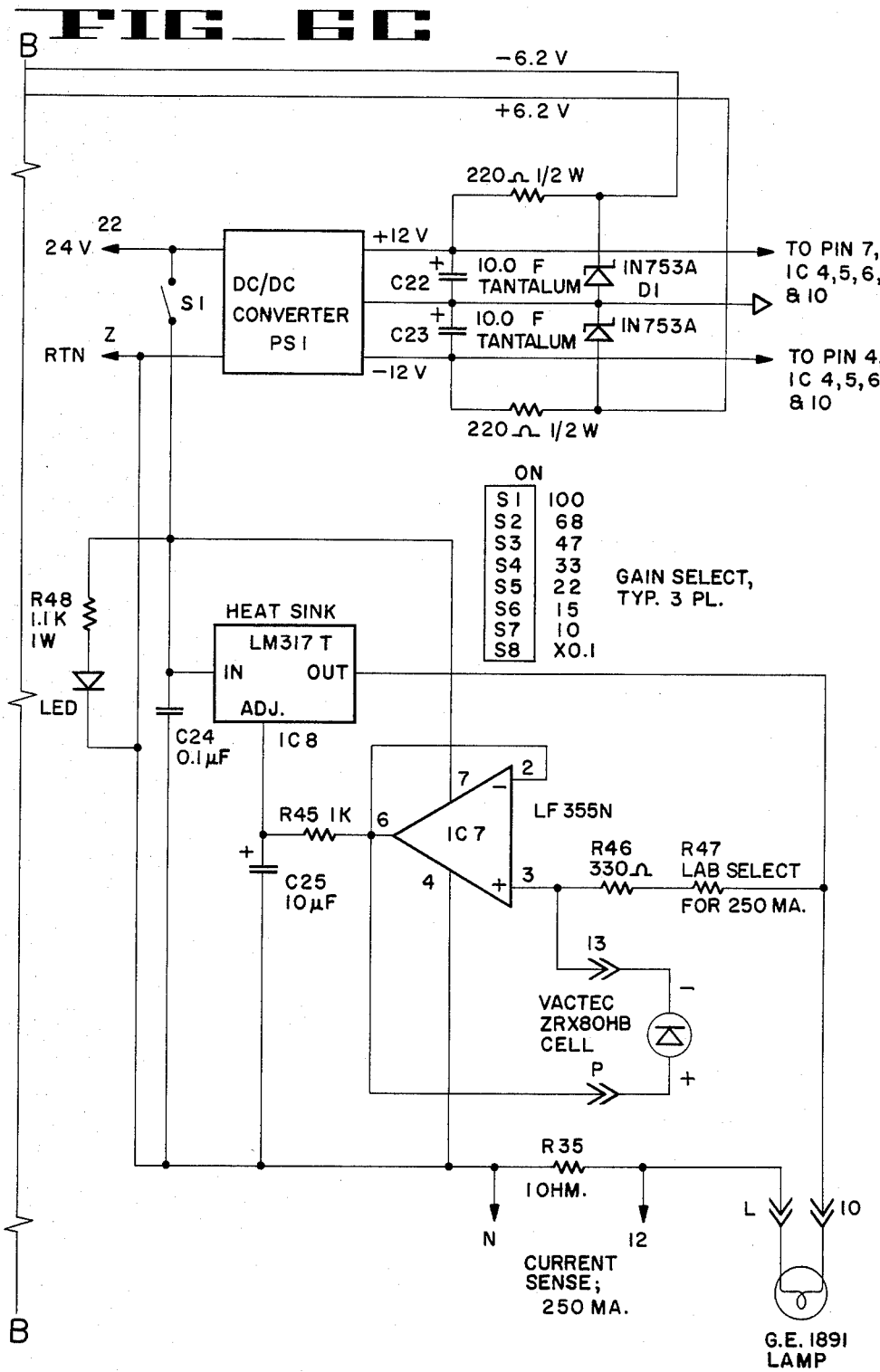
FIG_6C 4,519,710

1

COLORIMETER

TECHNICAL FIELD

This invention relates to colorimetric apparatus for real-time monitoring of an aqueous solution containing a colored ion.

DESCRIPTION OF THE PRIOR ART

Colorimetric techniques for monitoring ion concentration in an aqueous solution have not heretofore been amenable to real-time monitoring applications, as required in industrial processes. In general, colorimeters available in the prior art were designed to take discrete rather than continuous measurements, and generally required calibration prior to each measurement.

SUMMARY OF THE INVENTION

It is an object of the present invention to provide apparatus for colorimetrically monitoring ion concentration in an aqueous solution on a real-time basis.

It is a particular object of the present invention to provide colorimetric instrumentation for continuously measuring concentration of an ionic species in an aqueous solution used in an industrial process.

A colorimeter in accordance with the present invention comprises a source of optical radiation, a multi-chambered flow cell through which a solution containing an ionic species to be monitored can flow, and photodetector devices responsive to radiation transmitted through the solution in the chambers of the flow cell. The radiation source may be monochromatic, or alternatively may emit radiation over a broad optical spectrum and be used in combination with discrete bandpass filters on the individual flow-cell chambers. The photodetector devices generate electrical outputs proportional to the intensity of the radiation transmitted through the solution. Electronic circuitry responsive to the outputs of the photodetector devices maintains the intensity of the radiation emitted by the radiation source at a substantially constant value.

DESCRIPTION OF THE DRAWING

FIG. 1 is a partially cut-away perspective view of a colorimetric apparatus in accordance with the present invention.

FIG. 2 is a plan view of the colorimetric apparatus shown in FIG. 1.

FIG. 5 is a schematic representation of the flow path of aqueous solution through the colorimetric apparatus of FIG. 1, together with a block diagram of electronic circuitry for monitoring ion concentration in the solution.

FIG. 6 (comprising FIGS. 6A, 6B and 6C) is a schematic representation of the electronic circuitry of FIG. 5.

BEST MODE OF CARRYING OUT THE INVENTION

Figure 4:
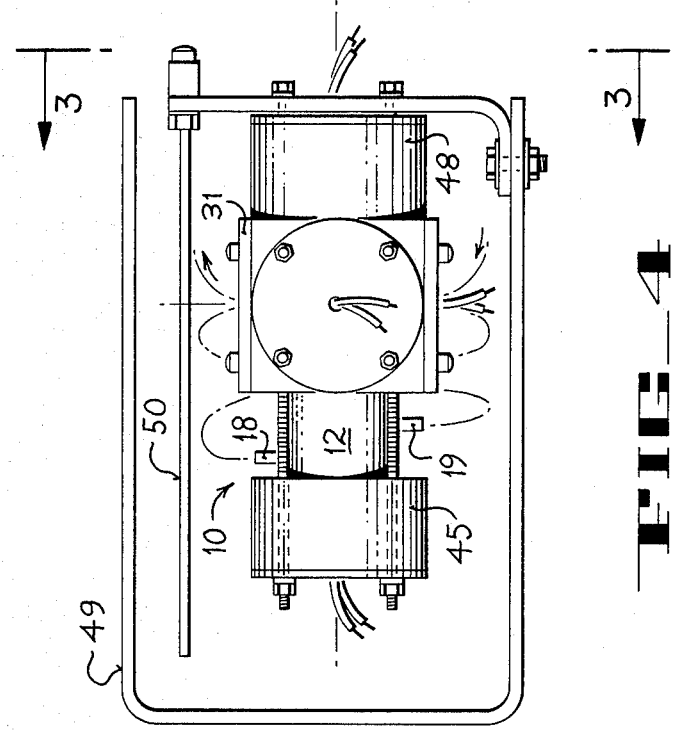
FIG. 4 is an elevation view of the colorimetric apparatus of FIG. 1 in a direction perpendicular to the view shown in FIG. 3.

A colorimeter in accordance with the preferred embodiment of the present invention comprises a three-chambered flow cell 10, which is shown in partially cut-away perspective view in FIG. 1 and in plan view in FIG. 2. The flow cell 10 is intended primarily for use in monitoring the concentration of a colored ion in an aqueous solution used in a continuous industrial process.

A "colored ion" is an ion that imparts a characteristic color to an aqueous solution: e.g., $Cr^{+6}$ characteristically turns the solution yellow, and $Cr^{+3}$ characteristically turns the solution blue. In the usual industrial application, there would be a continuous flow through the flow cell 10 of solution sample drawn from a reservoir or tank containing the solution whose colored ion concentration is to be monitored.

The colorimeter described herein does not absolutely require that the sample drawn from the solution reservoir be flowing through the flow cell 10 when ion concentration measurements are being made. in an appropriate application, the flow cell 10 could be filled with a first quantity of solution sample, and the ion concentration measurement could be made. Thereafter, the first quantity of solution sample would be flushed from the flow cell 10, and a second quantity of solution sample would be admitted for ion concentration measurement. This discontinuous measurement procedure could be repeated for successive samples drawn from the solution reservoir during the course of the industrial process. However, a continuous flow of solution sample through the flow cell 10 would take advantage of the continuous monitoring capability of an instrument according to the present invention, and would minimize sedimentation problems that are more likely to occur when the solution is not flowing.

With reference to FIGS. 1 and 2, the flow cell 10 is seen to comprise three interconnected flow chambers 11, 12 and 13. The sample of solution entering into the flow cell 10 from the reservoir passes via an inlet line 14 through an entrance orifice 15 in the bottom of the first flow chamber 11, and eventually fills the first chamber 11. The sample then passes out of the first chamber 11 through an exit orifice 16 at the top thereof, and flows via a conduit line 17 through an entrance orifice 18 in the bottom of the second flow chamber 12, and eventually fills the second chamber 12. Thereafter, the sample passes out of the second chamber 12 through an exit orfice 19 at the top thereof, and flows via a conduit line 20 through an entrance orifice 21 in the bottom of the third flow chamber 13, and eventually fills the third chamber 13. The sample then exits from the flow cell 10 by passing out of the third chamber 13 through an exit orifice 22 at the top thereof. (The exit orifice 22 is not visible in the perspective of FIG. 1, but is shown vertically aligned with the entrance orifice 21 in FIG. 2.) The sample exiting from the flow cell 10 returns to the solution reservoir via an outlet line 23.

Figure 3:
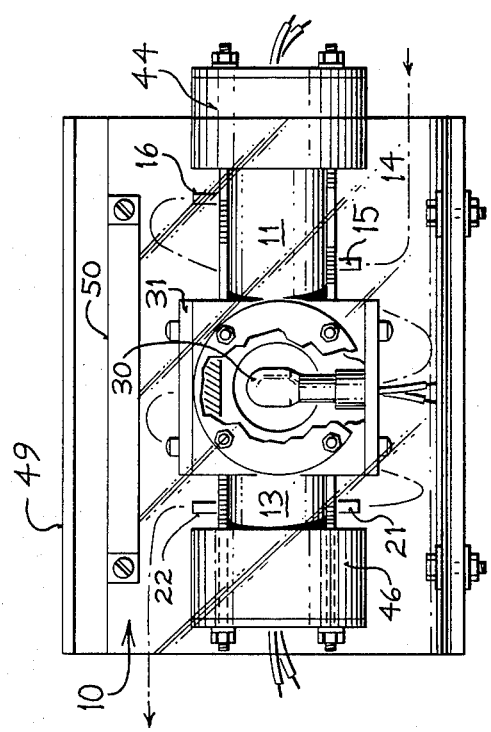
FIG. 3 is a partially cut-away elevation view showing the light source of the colorimetric apparatus of FIG. 1.
Figure 3:
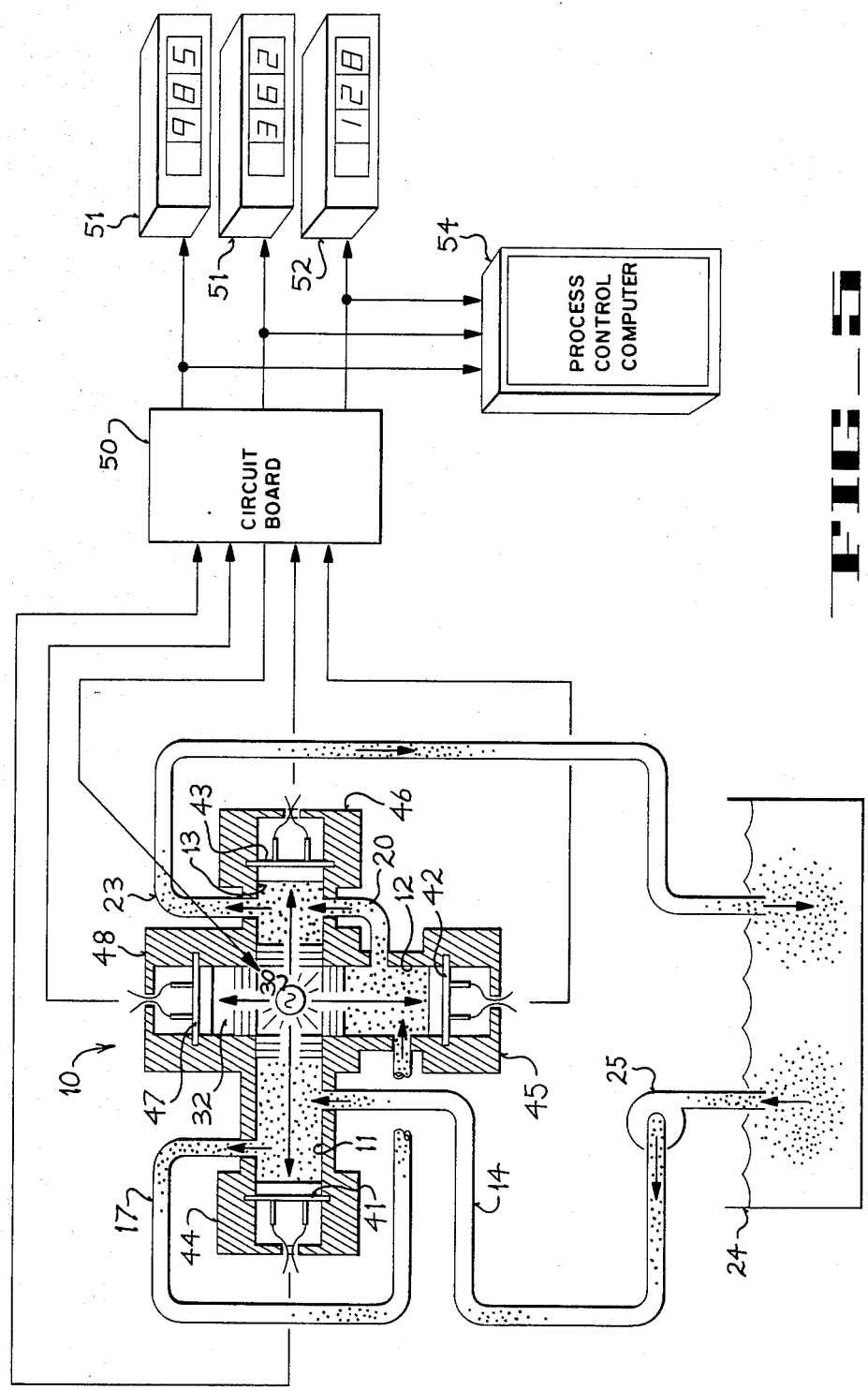

Partially cut-away elevation views of the flow cell 10 as seen from directions at a right angle to each other are shown in FIGS. 3 and 4. In FIG. 3, the flow chambers 11 and 13 appear in vertical cross section, while in FIG. 4 the flow chamber 12 appears in vertical cross section. The three flow chambers 11, 12 and 13 are of hollow circularly cylindrical configuration, and have the same diameter but different lengths. The reason for the different lengths is explained hereinafter. The ends of the flow chambers 11, 12 and 13 have fluid-tight covers that are transparent to optical radiation, as discussed hereinafter.

A schematic diagram illustrating the flow path of the solution sample passing through the flow cell 10 is shown in FIG. 5. The solution comprising the colored ion whose concentration is to be monitored is contained within a reservoir 24. The reservoir 24 could represent, for example, a bath into which articles are dipped for chemical treatment in the course of a manufacturing process. A sample of the solution is drawn by a pump 25 into the inlet line 14 for delivery to the first flow chamber 11 of the flow cell 10. The solution sample then flows from the first flow chamber 11 into the second flow chamber 12 via the conduit line 17, and from the second flow chamber 12 into the third flow chamber 13 via the conduit line 20. The solution sample is returned from the flow cell 10 to the reservoir 24 via the outlet line 23.

The colorimeter, as illustrated in FIGS. 1-5, also comprises a single regulated source 30 of optical radiation. The radiation source 30 is preferably an incandescent lamp (e.g., a General Electric Company lamp identified by catalog No. 1891) rated at 250 milliamperes. The lamp 30 is housed in a metal container 31 of generally cubical configuration with four windowed sidewalls. An end of each one of the flow chambers 11, 12 and 13 is positioned abutting a correponding one of three of the windowed sidewalls of the lamp container 31. An end of an empty cylindrical chamber 32 (i.e., a chamber not in the flow path of the solution sample passing through the flow cell 10) abuts a fourth windowed sidewall of the lamp container 31. The cylindrical flow chambers 11, 12 and 13 are preferably made of a heat-insulating plastic material such as an opaquely coated acrylic.

A heat-absorbing device 33 transparent to radiation emitted by the lamp 30 (e.g., a disc of tempered glass) is fitted in each of the windows in the sidewalls of the lamp container 31, as shown in FIG. 2. Depending upon the application, a lens 34 (e.g., a Fresnel lens) could be positioned between any one or more of the heat-absorbing discs 33 and the corresponding chambers 11, 12, 13 and 32 to collimate the radiation emitted by the lamp 30. Also, depending upon the particular application, an optical bandpass filter 35 or a plurality of such filters could be positioned between any one or more of the lenses 34 and the corresponding chambers 11, 12, 13 and 32.

Fluid-tight covers 36 are secured to the proximal ends of the flow chambers 11, 12 and 13 (i.e., the ends abutting the windows in the sidewalls of the lamp container 31). The flow-chamber covers 36 are transparent to radiation in the particular wavelengths permitted by the bandpass filters 35 to enter into the particular flow chambers 11, 12 and 13. The flow-chamber covers 36 could be made of an acrylic plastic material such as Lucite. An iris diaphragm 37 is preferably interposed between each band-pass filter 35 and flow-chamber cover 36 in order to collimate the radiation entering into the particular flow chamber 11, 12 or 13.

At the distal ends of the flow chambers 11, 12, and 13 (i.e., at the ends away from the lamp container 31), fluid-tight covers 38 are secured. The flow-chamber covers 38, like the covers 36 at the proximal ends, are transparent to radiation permitted to enter into the flow chambers. Photodetector devices 41, 42 and 43 are mounted in generally cylindrical housing structures 44, 45 and 46, respectively, which are secured to the distal ends of the corresponding cylindrically configured chambers 11, 12 and 13. The photodetector devices 41, 42 and 43, which are protected from stray light and thermal energy, preferably comprise selenium cells of the kind marketed by Vactec Corporation under catalog No. ZRX80HB. Preferably, an iris diaphragm 39 is interposed between each flow-chamber cover 38 and the corresponding photodetector device 41, 42 or 43 in order to collimate the radiation exiting from the particular flow chamber 11, 12 or 13.

The empty chamber 32 is formed by securing a photodetector device 47 mounted in a cylindrical housing structure 48 to the fourth windowed sidewall of the lamp container 31. The volume of the empty chamber 32 is defined by the generally cylindrical interior surface formed when the housing structure 48 abuts the lamp container 31 in alignment with the window in the sidewall, and by the proximal end surface provided by the bandpass filter 35 fitted into the window, and by a distal end surface provided by the photodetector device 47. It is preferable also to position an iris diaphragm 39 in the empty chamber 32 adjacent the photodetector device in order to collimate the radiation exiting from the empty chamber 32.

The chambers 11, 12, 13 and 32 with their attached photodetector housing structures 44, 45, 46 and 48 extend from the lamp container 31 to form a cross-like structure having arms of unequal length. This cross-link structure is enclosed in a casing 49, which could be made of any metallic or plastic material suitable as an instrument casing. For prototype purposes, the casing 49 has been made of clear acrylic plastic.

In operation, as a sample of the solution whose ion concentration is to be monitored flows through the flow cell 10, radiation from the lamp 30 passes longitudinally through each of the flow chambers 11, 12 and 13, and through the empty chamber 32, to the corresponding photodetector devices 41, 42, 43 and 47. As noted above, the flow chambers 11, 12 and 13 are of different lengths. Consequently, radiation transmitted through the solution sample in the three different flow chambers 11, 12 and 13 travels through a greater or lesser quantity of the solution sample depending upon the length of the particular flow chamber. Depending upon the radiation absorption characteristics of the solution with respect to the wavelength or wavelengths emitted by the lamp 30, the intensity of the transmitted radiation reaching the photodetector devices 41, 42 and 43 in general varies according to the length of the flow chambers 11, 12 and 13, respectively.

As discussed more fully hereinafter, the intensity of the radiation reaching the photodetector device 47 at the distal end of the empty chamber 32 controls the intensity of the radiation emitted by the lamp 30. The fact that the radiation transmitted through the three flow chambers 11, 12 and 13 emanates from a single intensity-regulated radiation source (i.e., from the lamp 30) assures uniformity of intensity calibration for the photodetector devices 41, 42 and 43.

The fact that many ionic species in aqueous solution have characteristic colors (i.e., absorb radiation at characteristic wavelengths) enables precise ion concentration measurements to be made colorimetrically. With the colorimeter of the present invention, each of the photodetector devices 41, 42 and 43 produces an electrical current output that is proportional to the intensity of the radiation transmitted through the corresponding flow chamber 11, 12 or 13. The intensity of the radiation at a given wavelength transmitted through a particular flow chamber 11, 12 or 13 is in turn proportional to the quantity of radiation-absorbing ion present in the solution sample flowing through that particular flow chamber 11, 12 or 13. The density of the solution sample, and hence the concentration of a particular ionic species in the solution, is substantially uniform from one flow chamber 11, 12 or 13 to another. Therefore, any difference in intensity of the radiation reaching the different photodetector devices 41, 42 and 43 can be attributed solely to the difference in length of the different flow chambers 11, 12 and 13. Since the lengths of the flow chambers 11, 12 and 13 can be precisely known, the use of three different flow chambers of different lengths for making colorimeteric measurements provides a continuous real-time calibration check on the accuracy of the ion concentration measurement.

In an alternative application, the colorimeter of the present invention can be used for simultaneously measuring the concentrations of more than one ionic species in an aqueous solution. By providing bandpass filters for different wavelengths at the windows of different flow chambers, the photodetector devices at the distal ends of the different flow chambers can measure the radiation at different wavelengths transmitted through the solution sample passing through the flow cell 10.

The photodetector devices 41, 42, 43 and 47 and the radiation source 30 are interconnected by electronic circuitry as represented schematically in FIG. 6. The electronic circuitry can conveniently be contained on a circuit board 50, which is mounted in a conventional manner within the casing 49 as illustrated in FIGS. 1, 3 and 4. Electrical leads extending from the photodetector housing structures 44, 45, 46 and 48, as shown in FIGS. 1-4, are connected to input contacts on the circuit board 50, as illustrated diagrammatically in FIG. 5. Output contacts on the circuit board 50 are connected to electrical leads extending to devices such as millivoltmeters 51, 52 and 53, which visually display measurements indicating the radiation intensity detected by the photodetector devices 41, 42 and 43, respectively. The output contacts in the circuit board 50 can also be connected to a process control computer 54 for controlling the ion concentration of the solution in the reservoir 24.

The electronic circuitry on the circuit board 50, as illustrated in schematic detail in FIG. 6, contains noteworthy features which enable sophisticated functions to be performed in a minimum of space using a minimum of electronic components. FIG. 6 comprises FIGS. 6A, 6B and 6C, which are drawn on separate sheets of paper to permit the various components of the circuitry to be described in detail. Each selenium photodetector cell 41, 42 and 43 shown in FIG. 6A is connected to a corresponding chopper-stabilized IC (integrated circuit) operational amplifier (identified in the drawing by Intersil, Inc. catalog No. ICL7650CPD). Each chopper-stabilized operational amplifier is configured by means of feedback resistors to form a current-to-voltage conversion subcircuit. The output from each of these current-to-voltage conversion subcircuits is a voltage signal that is linearly proportional to the intensity of the radiation incident upon the corresponding photodetector cell.

The output of each current-to-voltage conversion subcircuit is scaled by a corresponding conventional operational amplifier in conjunction with a plurality of selectable gain-setting resistors, as shown in FIG. 6B. The "scaling" operational amplifiers are identified in the drawing by the industry-wide designation "741". The gain-setting resistors provide switch-selectable gains, thereby permitting scaling of the gain over a wide voltage range to obtain any desired amplification.

As illustrated in FIG. 6B, seven switches (labelled $S_1$ through $S_7$ in the drawing) are connectable to each "scaling" operational amplifier. These seven switches permit thirteen possible switch combinations, where the change in gain provided by each successive switch is fifty percent (50%) of the change in gain provided by the previous switch. The switch-selection technique made possible by this circuitry for changing gain in incremental steps of 50% is preferable to the traditional practice of using a potentiometer to provide a linearly increasing or decreasing gain.

With the 50% gain increments provided by switches $S_1$ through $S_7$, fine control of the gain of each "scaling" operational amplifier can be obtained at low amplification. Such fine control can not practicably be obtained using a linear potentiometer. Furthermore, the switch-selection technique of the present invention permits absolute repeatability in the selection of gain values. Repeatability could not be obtained with precision using a potentiometer, unless a calibration procedure were employed.

A monolithic voltage regulator (identified in FIG. 6C by National Semiconductor Corporation catalog No. LM317T) is used to adjust the intensity of the lamp 30 so as to maintain a substantially constant radiation intensity entering the flow cells 11, 12 and 13. The photodetector device 47 at the distal end of the empty chamber 32 generates a current that serves as a monitor signal indicating the actual intensity of the radiation emitted by the lamp 30. A current-setting resistor (labelled "Lab Select" in FIG. 6C) establishes a reference signal for determining the desired level of radiation intensity for the lamp 30. A limiting resistor (i.e., the 330 ohm resistor in FIG. 6C) is preferably placed in series with the current-setting resistor to prevent excess current from being driven through the lamp 30 during the "lab select" process.

A buffer amplifier (labelled IC7 in FIG. 6C) senses any difference between the monitor signal generated by the selenium cell 47 and the reference signal generated by the current-setting resistor. If the monitor signal and the reference signal are substantially equal, the monolithic voltage regulator maintains a constant lamp voltage. However, whenever the monitor signal differs from the reference signal by a predetermined amount, the monolithic voltage regulator generates an appropriate voltage output to adjust the intensity of the lamp 30.

A particular embodiment has been described herein for a colorimeter in accordance with the present invention. However, other embodiments suitable for particular applications would become apparent to workers skilled in the art upon perusal of the foregoing specification and accompanying drawing. Thus, the description presented herein is to be understood as illustrative of the invention, which is more generally defined by the following claims and their equivalents.

We claim:

1. A colorimeter for continuously measuring concentration of an ionic species in an aqueous solution, said colorimeter comprising:
    (a) a source of optical radiation;
    (b) a plurality of flow chambers through which a sample of said solution can pass, said flow chambers being interconnected so that said sample of said solution passes through each of said flow chambers in succession, each of said flow chambers admitting radiation from said source into said sample simultaneously, said flow chambers being configured so that said radiation from said source is transmitted through a different quantity of said sample in each flow chamber;

(c) a plurality of first photodetectors, each one of said first photodetectors being responsive to intensity of radiation from said source transmitted through said sample in a corresponding one of said flow chambers, each one of said first photodetectors generating an electrical output indicative of the concentration of said ionic species in said sample of said solution in said corresponding one of said flow chambers, electrical outputs from said plurality of first photodetectors being generated simultaneously;

(d) a second photodetector responsive to intensity of radiation emitted by said source; and (e) electronic circuitry interconnecting said radiation source and said second photodetector, said circuitry maintaining the intensity of said radiation emitted by said source at a substantially constant value.

2. The colorimeter of claim 1 wherein said radiation source is housed in a container having windowed sidewalls, each of said flow chambers being of generally cylindrical configuration, a first end of each of said flow chambers being positioned adjacent a corresponding windowed sidewall of said radiation source container.

3. The colorimeter of claim 2 wherein each one of said first photodetectors is positioned at a second end of a corresponding one of said cylindrically configured flow chambers.

4. The colorimeter of claim 1 further comprising means for gathering said radiation from said source into a plurality of collimated beams for admission into said sample of said solution in a corresponding one of said flow chambers.

5. The colorimeter of claim 2 further comprising lens means interposed between the first end of at least one of said flow chambers and said radiation source to collimate said radiation admitted into said sample of said solution in said one of said flow chambers.

6. The colorimeter of claim 1 further comprising optical filter means interposed between said radiation source and at least one of said flow chambers.

7. The colorimeter of claim 2 further comprising a bandpass filter interposed between the first end of at least one of said flow chambers and the corresponding windowed sidewall of said radiation source container.

8. The colorimeter of claim 3 wherein each one of said first photodetectors comprises a photovoltaic cell having a current output response that is substantially linearly proportional to intensity of said radiation transmitted through said sample of said solution in said corresponding one of said flow chambers.

9. The colorimeter of claim 1 wherein each one of said first photodetectors generates an electrical current output that serves as input to a current-to-voltage converter, said current-to-voltage converter comprising an operational amplifier producing an electrical voltage output that is linearly proportional to the intensity of said radiation transmitted through said sample of said solution in said corresponding one of said flow chambers.

10. The colorimeter of claim 9 wherein said operational amplifier is chopper-stabilized.

11. The colorimeter of claim 9 wherein said voltage output of said operational amplifier serves as input to a network of switch-selectable gain-setting resistors.

12. The colorimeter of claim 11 wherein said network of gain-setting resistors comprises a first resistor and a plurality of other resistors, each of said other resistors being greater in value than said first resistor by a whole number multiple of 50%, each of said other resistors having a different value than any other of said other resistors.

13. The colorimeter of claim 8 wherein said electronic circuitry comprises:

(a) means for generating a monitor signal proportional to the intensity of said radiation emitted by said source;

(b) means for generating a reference signal;

(c) amplifier means responsive to said monitor signal and to said reference signal for establishing a power level at said radiation source, said power level controlling the intensity of said radiation emitted by said source at said substantially constant value, thereby maintaining said monitor signal substantially equal to said reference signal.

* * * * *